(12) United States Patent
Ghelli et al.

(10) Patent No.: US 12,078,176 B2
(45) Date of Patent: Sep. 3, 2024

(54) MAGNETIC DRIVE CENTRIFUGAL PUMP

(71) Applicant: EUROSETS S.R.L., Medolla (IT)

(72) Inventors: Nicola Ghelli, Medolla (IT); Paolo Fontanili, Medolla (IT); Edgardo Costa Maianti, Medolla (IT)

(73) Assignee: EUROSETS S.R.L., Medolla (IT)

( * ) Notice: Subject to any disclaimer, the term of this patent is extended or adjusted under 35 U.S.C. 154(b) by 731 days.

(21) Appl. No.: 17/285,073

(22) PCT Filed: Oct. 16, 2019

(86) PCT No.: PCT/IB2019/058826
§ 371 (c)(1),
(2) Date: Apr. 13, 2021

(87) PCT Pub. No.: WO2020/079613
PCT Pub. Date: Apr. 23, 2020

(65) Prior Publication Data
US 2022/0023612 A1 Jan. 27, 2022

(30) Foreign Application Priority Data
Oct. 16, 2018 (IT) .................. 102018000009500

(51) Int. Cl.
*F04D 13/02* (2006.01)
*F04D 1/06* (2006.01)
(Continued)

(52) U.S. Cl.
CPC ....... *F04D 13/025* (2013.01); *F04D 13/0606* (2013.01); *F04D 29/426* (2013.01);
(Continued)

(58) Field of Classification Search
CPC .. F04D 13/025; F04D 13/0606; F04D 29/425; F04D 29/628; A61M 60/232; F05D 2260/33; F05D 2260/36
See application file for complete search history.

(56) References Cited

U.S. PATENT DOCUMENTS 4,984,974 A * 1/1991 Naya ............... F04C 27/009
277/350
6,152,704 A * 11/2000 Aboul-Hosn ........... F04D 13/04
604/151

(Continued)

FOREIGN PATENT DOCUMENTS

EP 2674624 A1 12/2013
JP H03286775 A 12/1991

*Primary Examiner* — Charles G Freay
(74) *Attorney, Agent, or Firm* — ASLAN LAW, P.C.

(57) ABSTRACT

A locking device having at least one load-bearing element, a first locking device engageable in a removable manner with the hollow body to lock it in travel with respect to the load-bearing element, the hollow body being movable in rotation around the axis with respect to the load-bearing element, and second locking device engageable in a removable manner with the support element, the locking device being movable between at least one release configuration and at least one locking configuration, wherein the second locking device engage with the support element to secure the load-bearing element in travel with respect thereto, the hollow body being movable in rotation around the axis with respect to the support element with the locking device in the locking configuration.

20 Claims, 4 Drawing Sheets

(51) Int. Cl.
*F04D 13/06* (2006.01)
*F04D 29/42* (2006.01)
*F04D 29/62* (2006.01)
*A61M 60/232* (2021.01)

(52) U.S. Cl.
CPC ......... *F04D 29/628* (2013.01); *A61M 60/232* (2021.01); *F05D 2260/33* (2013.01); *F05D 2260/36* (2013.01)

(56) References Cited

U.S. PATENT DOCUMENTS

| | | | |
|---|---|---|---|
| 8,985,969 B2* | 3/2015 | Hoshi | F04D 13/02 417/423.15 |
| 2006/0222533 A1* | 10/2006 | Reeves | A61M 1/3666 417/423.1 |
| 2010/0280305 A1* | 11/2010 | Hidaka | F04D 29/047 600/16 |
| 2014/0205480 A1 | 7/2014 | Nakano | |
| 2022/0025896 A1* | 1/2022 | Ghelli | A61M 60/806 |

* cited by examiner

MAGNETIC DRIVE CENTRIFUGAL PUMP

CROSS-REFERENCE TO RELATED APPLICATIONS

This application claims priority to IT Patent Application No. 102018000009500 filed on Oct. 16, 2018, and this application claims priority to and is a 371 of international PCT Application No. PCT/IB2019/058826 filed on Oct. 16, 2019, the entire contents of which are hereby incorporated by reference.

TECHNICAL FIELD

The present invention relates to a magnetic drive centrifugal pump.

BACKGROUND ART

The magnetic drive centrifugal pumps used in the biomedical sector are generally composed of an internally hollow body, provided with at least one blood inlet connector and one blood outlet connector, inside which is housed a rotor element provided with a plurality of blades adapted to convey, as a result of the rotation of the rotor element itself, the incoming blood towards the outlet connector.

The rotor element comprises a portion of magnetic material, and outside the hollow body a stator element is positioned which is adapted to define at least one magnetic field for controlling the rotor element in rotation inside the hollow body.

The rotor element can be kept raised with respect to the bottom of the hollow body by one or more bearings or by a magnetic field generated by the stator element, in the latter case reference is made to magnetic levitation pumps.

In particular, the stator element comprises a plurality of windings intended to be crossed by the electric current for the formation of one or more magnetic fields adapted to interact with the rotor element to raise it and bring it into rotation around the relevant axis.

Such windings are generally housed inside a relevant containment body adapted to couple with the hollow body containing the rotor element.

In particular, the hollow body containing the rotor element is generally fixed in a removable way to the containment body containing the stator element.

The stator and the relevant containment body are of the multiuse type, while the hollow body and the rotor contained therein are of the disposable type.

In other words, after each use on a patient, the hollow body and the rotor are replaced while the stator and the relevant containment body are reused.

Centrifugal pumps of known type do have a plurality of drawbacks.

The fixing of the hollow body to the containment body is generally carried out by means of mutual locking elements applied to the containment body itself, such as threaded elements or the like.

The fixing of the hollow body to the containment body is therefore not easy, as it requires having to individually intervene on each locking element.

This operation can also be complex due to the difficult access to the locking elements themselves.

Another drawback is that the locking elements must undergo maintenance jobs so as to ensure that they function properly over time.

Yet another drawback of magnetic drive pumps of known type is that they do not allow the easy adjustment of the angular position of the hollow body and, therefore, of the relevant outlet connector, with respect to the containment body.

If the outlet connector is difficult to access, the connection with the relevant blood outflow line is more complex, and this can result in the need to modify or lengthen the outflow line itself, as well as the risk of this line becoming blocked or damaged, thus compromising its operation.

DESCRIPTION OF THE INVENTION

The main aim of the present invention is to provide a magnetic drive centrifugal pump which enables the hollow body containing the rotor element to be easily and conveniently locked to the containment body inside which the stator element is housed and which, at the same time, enables the angular position of the outlet connector to be adjusted, in use, according to the specific requirements of the case, in order to facilitate connection with the relevant blood outflow line.

Within this aim, one object of the present invention is to provide a magnetic drive centrifugal pump which allows eliminating activities, and therefore also the relevant maintenance costs of the locking elements of the hollow body to the containment body.

Yet another object of the present invention is to allow easily adjusting the angular position of the hollow body and, therefore, of the relevant outlet connector.

Another object of the present invention is to devise a magnetic drive centrifugal pump which allows overcoming the aforementioned drawbacks of the prior art in the ambit of a simple, rational, easy, effective to use and low cost solution.

The aforementioned objects are achieved by the present magnetic drive centrifugal pump having the characteristics of claim 1.

BRIEF DESCRIPTION OF THE DRAWINGS

Other characteristics and advantages of the present invention will be more evident from the description of a preferred, but not exclusive, embodiment of a magnetic drive centrifugal pump, illustrated by way of a non-limiting example in the accompanying tables of drawing in which.

EMBODIMENTS OF THE INVENTION

Figure 1:
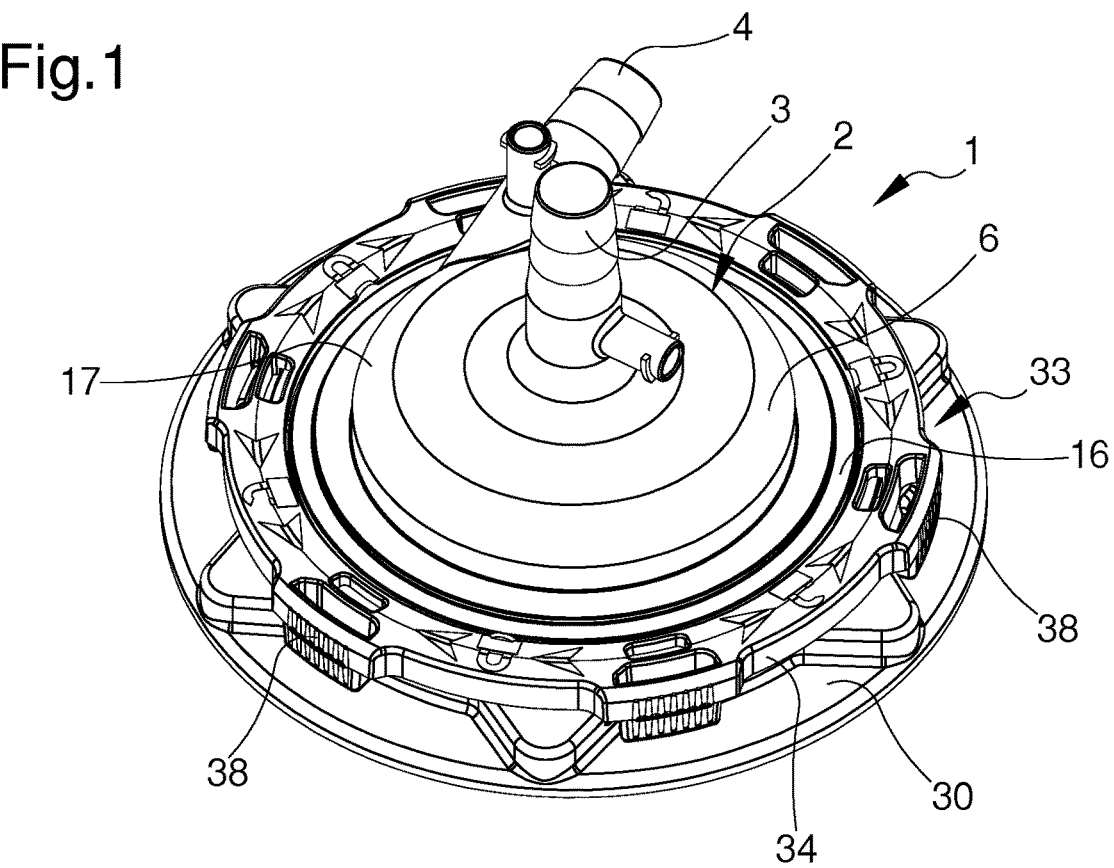
FIG. 1 is an axonometric view of a pump according to the invention with the locking element in the locking configuration.

With particular reference to these illustrations, reference numeral 1 globally indicates a magnetic drive centrifugal pump.

The pump 1 comprises at least one internally hollow body, identified in the figures by the reference numeral 2, provided with at least one inlet connector 3 for the venous blood coming from a patient and with at least one outlet connector 4 for the venous blood to be sent to a blood oxygenation device.

Preferably, the hollow body 2 comprises at least one lower element 5 and at least one upper element 6 separated from each other and mutually coupled.

The hollow body 2 therefore defines a volume 7, on which the inlet connector 3 and the outlet connector 4 face, in which at least one rotor element 8 is housed, provided with at least one portion made of magnetic material, identified in the figures with the reference numeral 9.

The rotor element 8 can be magnetically commanded in rotation around a relevant axis X, without contact, by a stator element (not shown in the figures), associable with the hollow body 2 and adapted to generate a magnetic field.

The ways of controlling the rotation of the rotor element 8, although not relating to the present invention, are widely known to the expert in the sector.

In particular, the stator element comprises a plurality of windings intended to be crossed by the electric current for the formation of one or more magnetic fields adapted to interact with the rotor element 8 to raise it and bring it in rotation around the relevant X axis.

In an alternative embodiment, not shown in the illustrations, the stator element can only be adapted to bring the rotor element 8 in rotation without contact, i.e. by means of the magnetic field generated by it, and the rotor element 8 is kept raised by a relevant bearing.

More specifically, the rotor element 8 comprises a revolving body 10, provided with a plurality of blades 11 arranged on it in a radial pattern and adapted to contact the blood entering the volume 7 to push it towards the outlet connector 4.

Advantageously, the revolving body 10 has an upper surface 26, facing upwards in use, with a concave shape. More in detail, the upper surface 26 has a substantially curvilinear extension so as to accompany the flow of blood in its fall into the volume 7 through the inlet connector 3, so as to reduce the risk of damage due to the impact with the revolving body itself.

The revolving body 10 is also provided with a housing seat 12, defined at its bottom portion, inside which is inserted the magnetic portion 9, closed underneath by a retaining element 13.

In addition, the lower element 5 has a housing 14 adapted to contain, in use, at least a portion of the revolving body 10, the blades 11 remaining outside the housing itself, which has a bottom wall 14a provided with a guiding member 14b, defined at the axis of rotation X, for the centering of the rotor element 8. More in detail, the revolving body 10 has a sleeve 10a that fits inside the relevant holes 15 obtained in the magnetic portion 9 and in the retaining element 13; following the insertion of the rotor element 8 inside the housing 14, the lower end of the sleeve 10a is fitted over the guiding member 14b coaxially to the axis of rotation X.

The upper element 6 has at least one perimeter flange 16 for coupling to the lower element 5 and at least one substantially dome-shaped body, identified in the illustrations by the reference numeral 17, which protrudes from the perimeter flange 16, where the outlet connector 4 is associated with the dome-shaped body 17.

Advantageously, the perimeter flange 16 defines a coupling surface 16a with the lower element 5 and the outlet connector 4 is raised with respect to the coupling surface 16a.

Preferably, the coupling surface 16a is substantially flat.

Between the outlet connector 4, which has an elongated shape, and the perimeter flange 16, an air space 18 is defined, inside which means can be inserted to tighten the upper element 6 and the lower element 5 during the sealing operations.

Appropriately, between the coupling surface 16a and the lower element 5 are placed sealing means 19, e.g., of the O-ring type.

Figure 2:
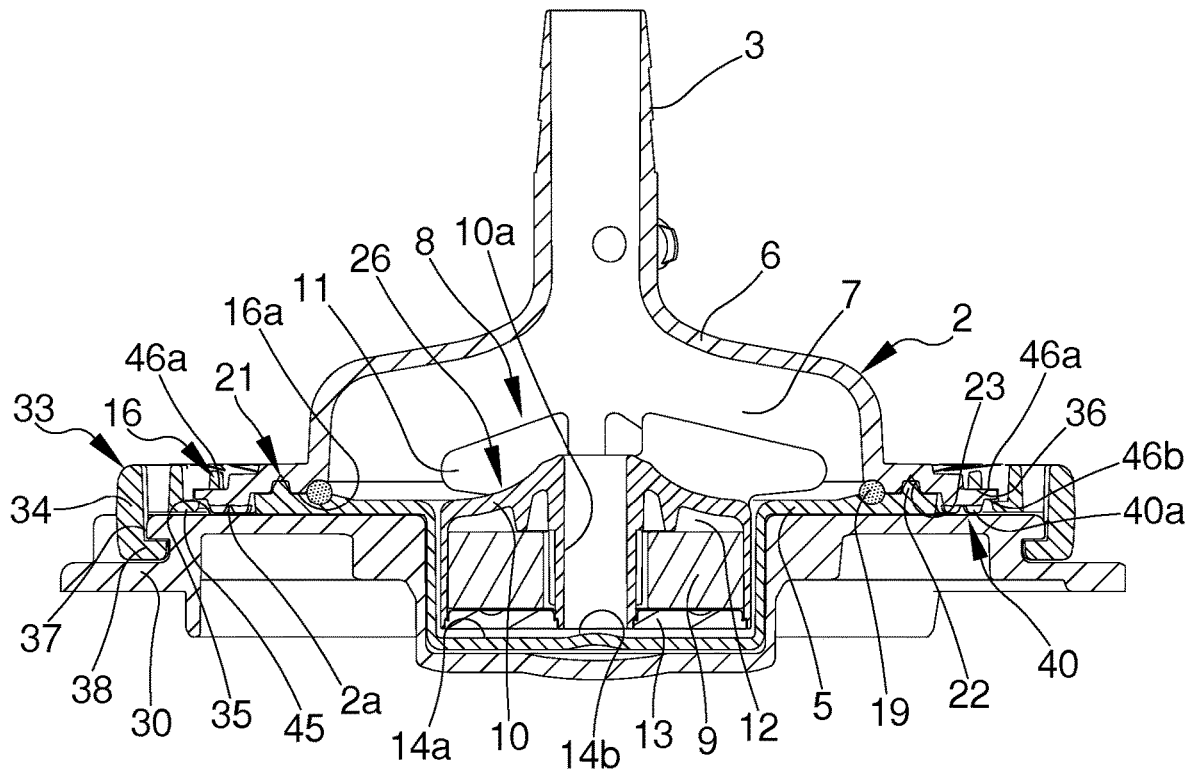
FIG. 2 is a cross-sectional view of the pump of FIG. 1.
Figure 3:
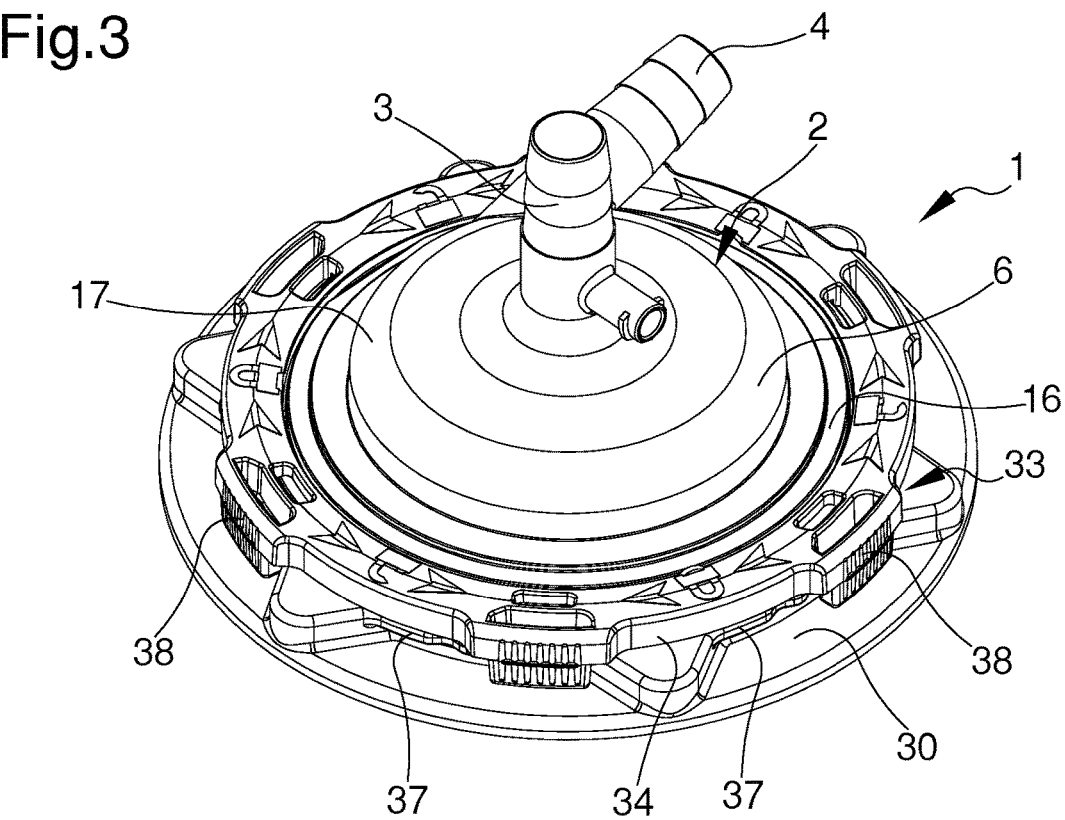
FIG. 3 is an axonometric view of a pump according to the invention with the locking element in the release configuration.
Figure 4:
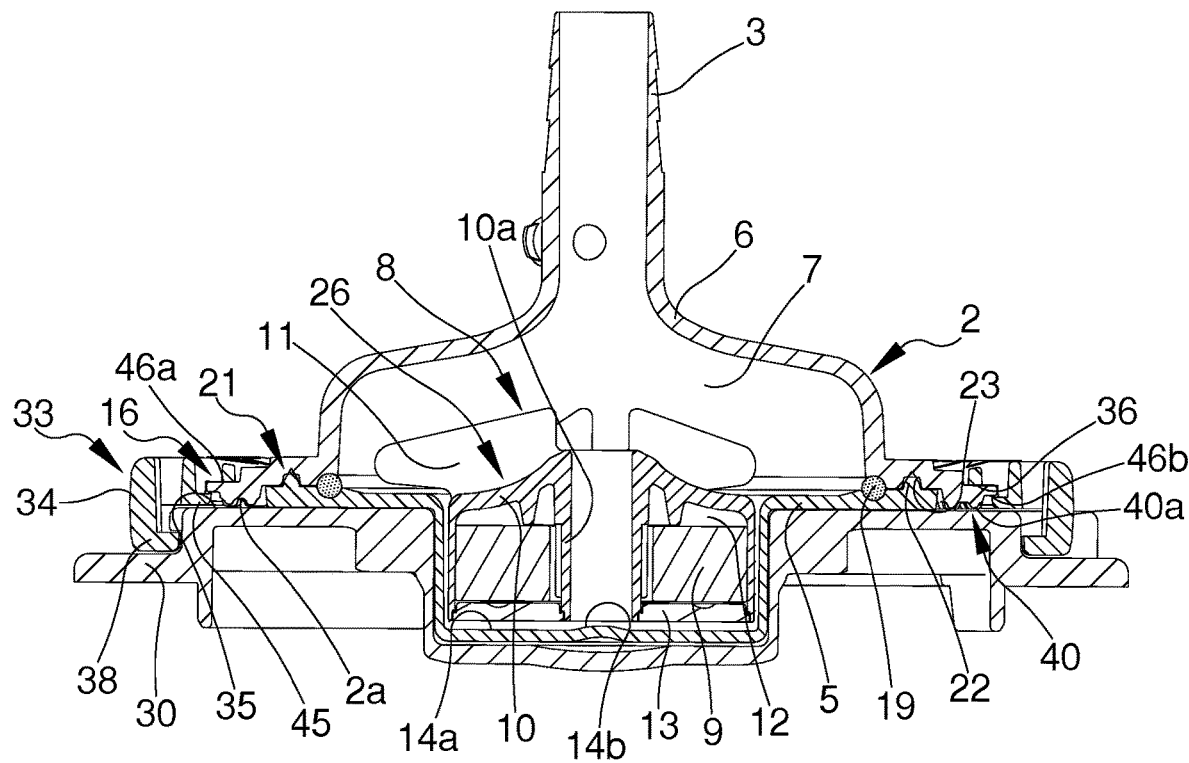
FIG. 4 is a cross-sectional view of the pump of FIG. 3.
Figure 5:
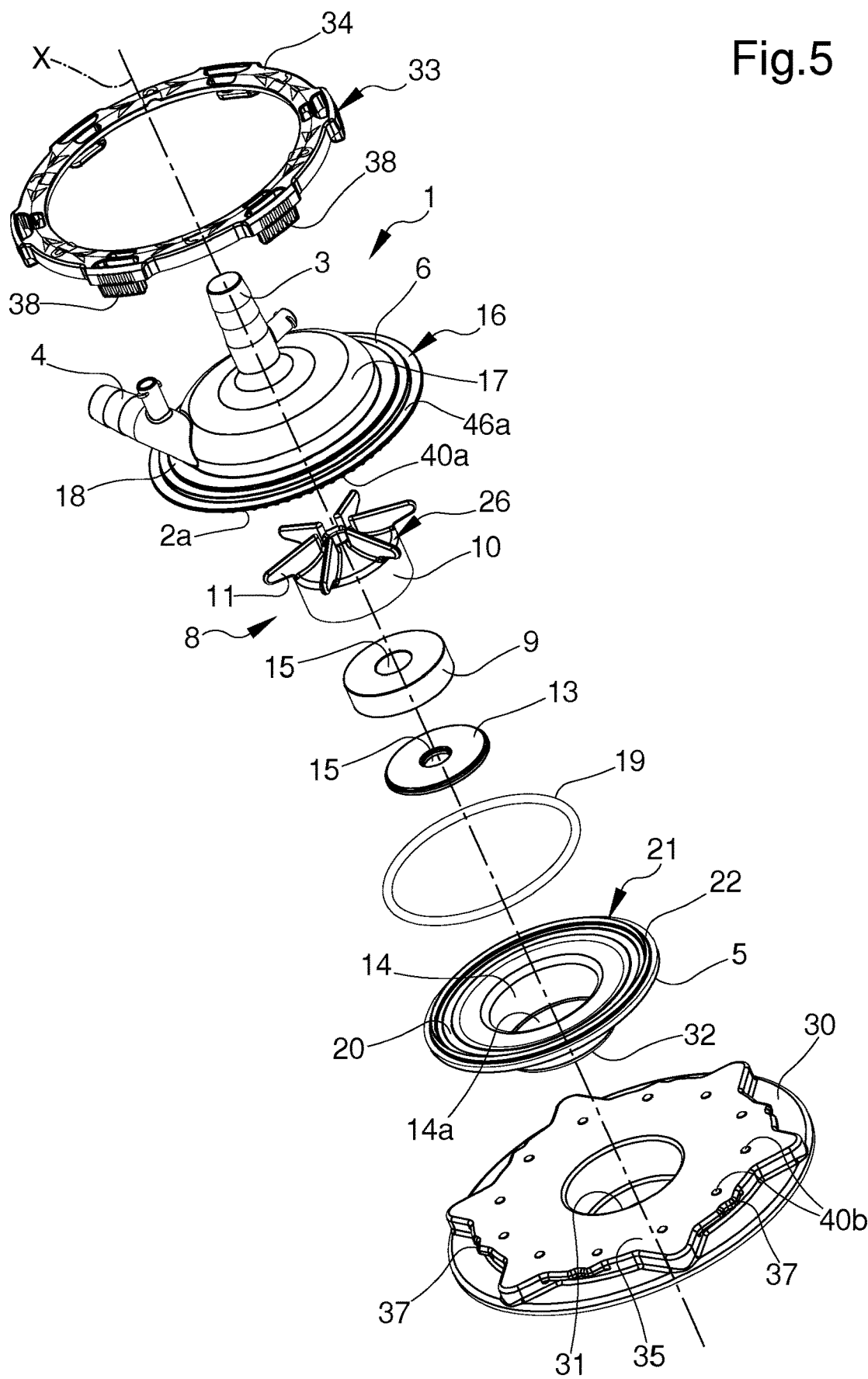
FIG. 5 is an exploded view of the pump according to the invention.
Figure 6:
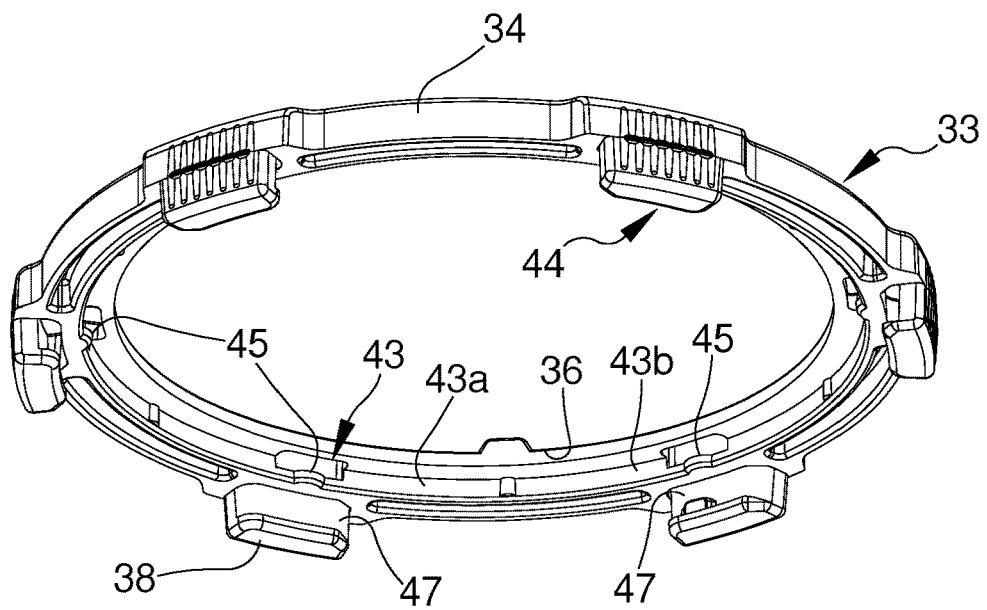
FIG. 6 is an axonometric view from below of the pump locking means of FIG. 1.
Figure 7:
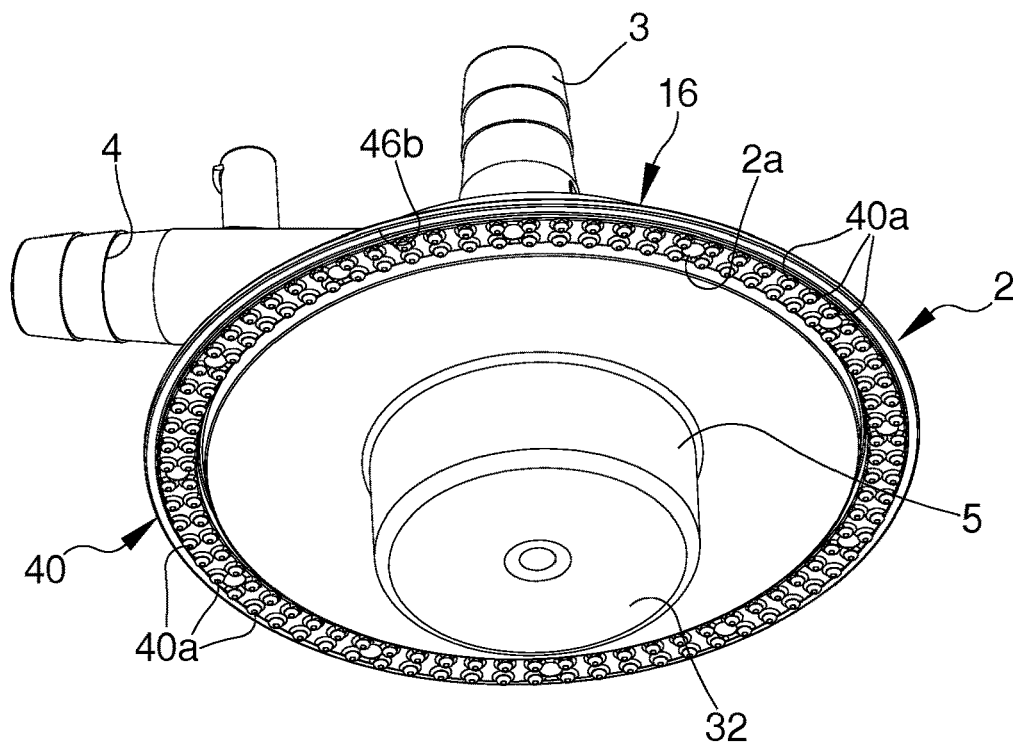
FIG. 7 is an axonometric view from below of the hollow body of the pump of FIG. 1.

More in particular, as shown in FIG. 2, the O-ring 19 is placed at the inner edge of the coupling surface 16a and facing the volume 7 inside the hollow body 2.

The lower element 5 also comprises a groove 20 adapted to house the O-ring 19 to prevent the displacement thereof in use.

Preferably, the outlet connector 4 is oriented transversely with respect to the axis of rotation X.

More in detail, the outlet connector 4, having an elongated shape, is inclined with respect to the coupling surface 16a. The outlet connector 4 is also inclined with respect to a plane passing through the axis of rotation X.

In the preferred embodiment shown in the illustrations, the inlet connector 3 is positioned at the top of the upper element 6 and extends coaxially to the axis of rotation X.

Appropriately, the upper element 6 and the lower element 5 are provided with relevant centering means 21 adapted to ensure the correct mutual positioning.

More in detail, the centering means 21 comprise at least one relief 22 defined on one of either the coupling surface 16a or the lower element 5 and at least one recess 23 defined on the other of either the lower element 5 and the coupling surface 16a, where the relief 22 is adapted to insert itself into the recess 23 as a result of the positioning of the upper element 6 on the lower element 5.

Since in the preferred embodiment shown in the illustrations, the upper element 6 and the lower element 5 have a substantially circular section, the recess 23 and the relief 22 have a substantially annular extension.

The centering means 21, and in particular the relief 22 and the recess 23, can operate as sealing means as a result of mutual locking, e.g. by sealing and/or gluing. The relief 22 and the recess 23 can therefore provide the mechanical and/or hydraulic seal in the coupling between the lower element 5 and the upper element 6.

The sealing means may therefore comprise at least one of either the O-ring 19 or the centering means 21, or preferably comprise them both.

Appropriately, the centering means 21 are arranged downstream of the O-ring 19 proceeding from the volume 7 outwards.

The pump 1 then comprises at least one support element 30 of the hollow body 2 which can be associated with the stator.

Appropriately, the support element 30 comprises an indentation 31 adapted to house the bottom portion, identified in the illustrations by the reference numeral 32, of the hollow body 2.

According to the invention, the pump 1 comprises removable locking means 33 for locking the hollow body 2 to the support element 30 along at least one direction of travel, which means can be moved between at least one release configuration, wherein the hollow body 2 is disengaged from the support element 30, and at least one locking configuration, wherein the hollow body 2 is locked in travel to the support element 30.

The locking means 33 comprise at least a load-bearing element 34, first locking means 43 and second locking means 44 associated with the load-bearing element 34 where the first locking means 43 are engageable in a removable manner with the hollow body 2 to lock it in travel with respect to the load-bearing element 34 and where the second locking means 44 are engageable in a removable manner with the support element 30 to lock in travel the load-bearing element 34 with respect to the support element itself. In the release configuration, the second locking means 44 are therefore disengaged from the support element 30, so that the load-bearing element 34 can be moved at least in travel with respect to the support element itself, while in the locking configuration, the second locking means 44 engage with the support element 30 to secure the load-bearing element 34 in travel with respect thereto.

The hollow body 2 can be moved in rotation around the axis X with respect to the support element 30 in the locking configuration.

The hollow body 2 can also be moved in rotation around the axis X with respect to the load-bearing element 34 even when it is engaged with the first locking means 43, regardless of the configuration taken by the second locking means 44. The first locking means 43 lock in travel the hollow body 2 together with the load-bearing element 34.

Preferably, the load-bearing element 34 is locked together with the first locking means 43 and with the second locking means 44.

The load-bearing element 34 can therefore be moved in rotation around the axis X with respect to the support element 30 to move from the release configuration to the locking configuration and vice versa. In particular, to move from the locking configuration to the release configuration, the load-bearing element 34 is rotated in a first direction, while to move from the release configuration to the locking configuration, it is rotated in a second direction opposite to the first.

In the preferred embodiment shown in the illustrations, the load-bearing element 34 has an annular shape and is fitted over the hollow body 2, coaxially thereto.

Advantageously, the first locking means 43 are of the interlocking type.

More in particular, the first locking means 43 comprise at least one contrast surface 36 and one or more anchoring elements 45 arranged facing the contrast surface 36 in such a way as to define a first housing seat 43a inside which the edge of the perimeter flange 16 is fitted by interlocking.

The perimeter flange 16 in turn has a first holding surface 46a adapted to operate in conjunction with the contrast surface 36 and at least a second holding surface 46b, opposite the first holding surface 46a adapted to operate in conjunction with the anchoring elements 45.

The holding surfaces 46a and 46b are arranged transversely, and in particular perpendicularly, to the axis X. It follows, therefore, that, in use (i.e. as a result of the engagement with the hollow body 2) the contrast surface 36 and the anchoring elements 45 are also arranged transversely to the axis X.

As a result of the insertion into the first seat 43a, the perimeter flange 16 and, therefore, the hollow body 2, can be moved in rotation around the axis X and is locked in travel with respect to the load-bearing element 34 along at least the axis X.

The first locking means 43 also define a side wall 43b which secures in travel the hollow body 2 to the load-bearing element 34 along a direction transversal to the axis X.

The side wall 43b is placed between the contrast surface 36 and the anchoring elements 45 and delimits the first seat 43a laterally.

Appropriately, the contrast surface 36 is defined by the load-bearing element 34 and the first locking means 43 comprise a plurality of anchoring elements 45 angularly spaced away from each other on said load-bearing element 34. In particular, since the load-bearing element 34 has a substantially circular shape (i.e. except for the machining tolerances), the anchoring elements 45 are arranged on the load-bearing element 34 in a radial pattern.

The contrast surface 36 and the anchoring elements 45 are defined in a single body piece with the load-bearing element 34.

In the preferred embodiment shown in the illustrations, the support element 30 defines at least one projection 37 and the second locking means 44 are engaged with and disengaged from the projection 37 in the locking configuration and in the release configuration, respectively.

Advantageously, the second locking means 44 comprise at least one substantially C-shaped gripping element 38 so as to define a second housing seat 47 of the projection 37 in the locking configuration.

As a result of the insertion of the projection 37 inside the second seat 47, the support element 30 is locked with respect to the load-bearing element 34.

It follows that, as a result of the displacement of the locking means 33, and in particular of the load-bearing element 34, from the release configuration to the locking configuration, the insertion of the projection 37 inside the second seat 47 defined by the relevant gripping element 38 locks the support element 30 to the load-bearing element 34 and, therefore, to the hollow body 2 in turn secured in travel to the load-bearing element itself by effect of the engagement with the first locking means 43.

More in detail, the second locking means 44 comprise a plurality of gripping elements 38 angularly spaced apart from each other on the load-bearing element 34 and the support element 30 comprises a plurality of projections 37 angularly spaced apart from each other and insertable in a relevant gripping element 38 as a result of the displacement of the load-bearing element 34 from the release configuration to the locking configuration.

Appropriately, the gripping elements 38 are equal in number to the projections 37, so that each gripping element 38 engages with a corresponding projection 37 in the locking configuration.

Since both the load-bearing element 34 and the support element 30 have a substantially circular shape, the gripping elements 38 and the projections 37 are arranged in a radial pattern on the load-bearing element 34 and on the support element 30, respectively.

In the preferred embodiment shown in the illustrations, the hollow body 2 has an abutment surface 2a arranged, in use (i.e. during the use of pump 1), resting on a reference surface 35 defined by the support element 30.

Conveniently, the pump 1 comprises abutment means 40 adapted to identify the position of the hollow body 2 with respect to the support element 30. The abutment means 40 are also adapted to keep the hollow body 2 stationary with respect to the support element 30 during the displacement of the load-bearing element 34 between the release configuration and the locking configuration.

More particularly, the abutment means 40 comprise one or more first abutment elements 40a defined on the abutment surface 2a of the hollow body 2 and one or more second abutment elements 40b defined on the reference surface 35 of the support element 30, where the first abutment elements 40a are adapted to lean against the second abutment elements 40b.

Preferably, the abutment means 40 comprise a plurality of first abutment elements 40a angularly spaced from each other by a first angular range and a plurality of second abutment elements 40b angularly spaced from each other by a second angular range.

The first angular range differs from the second angular range and, in the embodiment shown in the illustrations, the first angular range is less than the second angular range.

As a result of the rotation of the hollow body 2 with respect to the support element 30, the first abutment elements 40a then contact in succession the second abutment elements 40b each time the hollow body 2 is rotated by an angle equal to the first angular range. This way, the user has an immediate response as to the magnitude of the rotation of the hollow body 2 with respect to the support element 30.

Moreover, once the desired angular position has been reached, when the load-bearing element 34 is displaced to move it from the release configuration to the locking configuration, due to the mutual contact between the first and second abutment elements 40a and 40b, the hollow body 2 maintains its angular position with respect to the support element 30.

Conveniently, at least one of either the first or the second abutment elements 40a, 40b, preferably both, is shaped as a hemisphere.

The operation of the present invention is as follows.

The load-bearing element 34 is initially fitted on the hollow body 2 so that the edge of the perimeter flange 16 engages with the first locking means 43.

In particular, the edge of the perimeter flange 16 is made to insert into the first seat 43a, thus being placed between the contrast surface 36 and the anchoring elements 45.

In this configuration, the hollow body 2 is free to rotate around the axis X with respect to the load-bearing element 34 and is secured in travel with respect thereto.

Subsequently, the bottom portion 32 of the hollow body 2 is inserted into the indentation 31 and the abutment surface 2a rests on the reference surface 35.

In this condition of use, the load-bearing element 34 is in release configuration, i.e. the second locking means 44 are disengaged from the support element 30. As a result of the movement of the load-bearing element 34 with respect to the support element 30, and in particular of its rotation around the axis X, the gripping elements 38 engage with the projections 37, which therefore enter the second seat 47.

Once the locking configuration has been reached, the support element 30 is then locked with the load-bearing element 34, which is in turn secured in travel to the hollow body 2. It follows, therefore, that the hollow body 2 is locked in travel together with the support element 30 by means of the locking means 33, and in particular by means of the load-bearing element 34.

In this configuration of use, the hollow body 2 can still rotate around the axis X with respect to the support element 30, and therefore with respect to the load-bearing element 34.

This rotation of the hollow body 2, which is marked by the mutual interaction of the abutment elements 40a, 40b, enables the operator to position the outlet connector 4 at will, choosing the most suitable orientation for the specific needs of the case, i.e. according to the connection with the relevant blood transport lines.

The contact between the first and second abutment elements 40a and 40b makes it possible to define a stable angular position, i.e. one not altered by the rotation of the load-bearing element 34.

Once the operation on the patient has been completed, the load-bearing element 34 is returned to the release configuration and the hollow body 2 is removed from the support element 30.

The hollow body 2, comprising the rotor element 8, and the load-bearing element 34 are then replaced with new ones for the subsequent treatment.

It has in practice been ascertained that the described invention achieves the intended objects and, in particular, the fact is underlined that the centrifugal pump to which the present invention relates, allows the hollow body in which the rotor element is housed to be easily locked to and removed from the support element of the stator element, and at the same time allows its rotation around the relevant axis so as to direct the outlet connector in the most suitable position for connection with the blood transport lines. This is made possible by the fact that the locking means are removable with respect to the support element and can therefore be removed and replaced together with the hollow body containing the rotor element and by the fact that they are adapted to secure in travel the hollow body to the support element, while leaving the hollow body free to rotate around its own axis with respect thereto.

This makes it considerably easier, compared to pumps of the known type, to connect the outlet connector to the relevant blood outflow line, thus reducing the risk of an interruption of the flow along the line and facilitating the filling of the downstream oxygenator.

The invention claimed is:

1. A magnetic drive centrifugal pump comprising:
at least one internally hollow body provided with at least one inlet connector and with at least one outlet connector for blood;
at least one rotor element, housed inside said at least one internally hollow body and provided with at least one portion made of magnetic material, said at least one rotor element being magnetically commanded in rotation around an axis, without contact, by a stator element associable with said at least one internally hollow body; and
at least one support element of capable of supporting said at least one internally hollow body wherein said at least one support element is associable with said stator element;
wherein the magnetic drive centrifugal pump comprises removable locking means wherein said removable locking means is capable of locking said at least one internally hollow body to said at least one support element and wherein said removable locking means locks a movement of said at least one internally hollow body with respect to said at least one support element along at least one direction, where said removable locking means comprise:
at least one load-bearing element,
first locking means engageable in a removable manner with said at least one internally hollow body, wherein said first locking means locks said at least one internally hollow body to said at least one load-bearing element along said at least one direction with respect to said at least one load-bearing element, wherein said at least one internally hollow body being movable in rotation around said axis with respect to said at least one load-bearing element when the first locking means is engaged with said at least one internally hollow body, and second locking means engageable in a removable manner with said at least one support element, said removable locking means being movable between at least one release configuration, wherein said second locking means are disengaged from said at least one support element and said at least one load-bearing element is movable along said at least one direction in travel-with respect to said at least one support element, and at least one locking configuration, wherein said second locking means engage with said at least one support element to secure said at least one load-bearing element along said at least one direction with respect thereto, said at least one internally hollow body being movable in rotation around said axis with respect to said at least one support element with said removable locking means in the locking configuration.

2. The magnetic drive centrifugal pump according to claim 1, wherein
said at least one load-bearing element is locked together with said first locking means and with said second locking means whereby said at least one load-bearing element, said first locking means and the said second locking means are integral to each other.

3. The magnetic drive centrifugal pump according to claim 2, wherein
said at least one load-bearing element is movable in rotation around said axis between the release configuration and the locking configuration.

4. The magnetic drive centrifugal pump according to claim 3, wherein
said at least one load-bearing element has an annular shape and is fitted over said at least one internally hollow body coaxially thereto.

5. The magnetic drive centrifugal pump according to claim 4, wherein
said first locking means are adapted to engage by interlocking with said at least one internally hollow body.

6. The magnetic drive centrifugal pump according to claim 5, wherein
said first locking means comprise at least one contrast surface and one or more anchoring elements arranged facing said at least one contrast surface in such a way as to define a first housing seat, said at least one internally hollow body comprising a perimeter flange an edge of which is capable of being inserted by interlocking into or inside said first seat.

7. The magnetic drive centrifugal pump according to claim 6, wherein
said perimeter flange is movable in rotation around said axis when said perimeter flange is inserted into or inside said first seat.

8. The magnetic drive centrifugal pump according to claim 7, wherein
said at least one contrast surface is defined by said at least one load-bearing element and said magnetic drive centrifugal pump comprises a plurality of said one or more anchoring elements positioned angularly spaced away from each other on said at least one load-bearing element.

9. The magnetic drive centrifugal pump according to claim 8, wherein
said perimeter flange comprises at least a first holding surface adapted to operate in conjunction with said at least one contrast surface and at least a second holding surface, opposite said first holding surface, adapted to operate in conjunction with said one or more anchoring elements.

10. The magnetic drive centrifugal pump according to claim 9, wherein
said first and second holding surfaces are arranged substantially perpendicularly to said axis of rotation.

11. The magnetic drive centrifugal pump according to claim 10, wherein
said at least one support element comprises at least one projection and that said second locking means is disengaged from said at least one projection in the release configuration and is engaged with the protrusion itself in the locking configuration.

12. The magnetic drive centrifugal pump according to claim 11, wherein
said second locking means comprise at least one substantially C-shaped gripping element, so as to define a second housing seat of said at least one projection in the locking configuration.

13. The magnetic drive centrifugal pump according to claim 12, wherein
said second locking means comprise a plurality of said at least one substantially C-shaped gripping elements angularly spaced apart from each other on said at least one load-bearing element and that said at least one support element comprises a plurality of said at least one projections angularly spaced apart from each other and insertable in a relevant gripping element as a result of the displacement of said at least one load-bearing element to the locking configuration.

14. The magnetic drive centrifugal pump according to claim 13, wherein
said at least one load-bearing element and said at least one support element have a substantially circular extension, and
said at least one substantially C-shaped gripping elements and said plurality of said at least one projections are arranged in a radial pattern on said at least one load-bearing element and on said at least one support element, respectively.

15. The magnetic drive centrifugal pump according to claim 14, wherein
said at least one internally hollow body has at least one abutment surface arranged resting on a reference surface defined by said at least one support element.

16. The magnetic drive centrifugal pump according to claim 15, further comprising:
abutment means adapted to keep said at least one internally hollow body stationary with respect to said at least one support element during the displacement of said at least one load-bearing element between the release configuration and the locking configuration.

17. The magnetic drive centrifugal pump according to claim 16, wherein
said abutment means comprise one or more first abutment elements defined on said at least one abutment surface and one or more second abutment elements defined on said reference surface, and
said one or more first abutment elements being adapted to come into physical contact with said one or more second abutment elements.

18. The magnetic drive centrifugal pump according to claim 17, wherein
said abutment means comprise a plurality of said one or more first abutment elements spaced from each other by a first angular range and comprise a plurality of said one or more second abutment elements spaced from each other by a second angular range other than said first angular range.

19. The magnetic drive centrifugal pump according to claim 18, wherein
at least one of either said first one or more abutment elements or said second one or more abutment elements is shaped as a hemisphere.

20. The magnetic drive centrifugal pump according to claim 1, wherein
said at least one load-bearing element is movable in rotation around said axis between the release configuration and the locking configuration.

* * * * *